(12) United States Patent
Hong et al.

(10) Patent No.: US 7,666,390 B2
(45) Date of Patent: Feb. 23, 2010

(54) DTPA DERIVATIVES AND METAL COMPLEXES THEREOF, AND RADIATION SOURCE AND CONTRAST AGENT INCLUDING THE METAL COMPLEXES

(75) Inventors: Young-Don Hong, Daejeon-si (KR); Sun-Ju Choi, Daejeon-si (KR); Ok Ja Choi, Jeonju-si (KR)

(73) Assignee: Korea Atomic Energy Research Institute, Daejon-Si (KR)

( * ) Notice: Subject to any disclaimer, the term of this patent is extended or adjusted under 35 U.S.C. 154(b) by 618 days.

(21) Appl. No.: 11/411,643

(22) Filed: Apr. 25, 2006

(65) Prior Publication Data

US 2006/0251583 A1    Nov. 9, 2006

(30) Foreign Application Priority Data

May 3, 2005    (KR) .................... 10-2005-0037062

(51) Int. Cl.
A61K 51/00    (2006.01)
A61K 49/04    (2006.01)
A61M 36/14    (2006.01)
A61B 5/055    (2006.01)
C07F 5/00    (2006.01)

(52) U.S. Cl. .................. 424/1.45; 424/1.11; 424/1.65; 424/9.3; 424/9.36; 424/9.364; 424/9.365; 424/9.4; 424/9.45; 424/9.451; 424/9.453; 424/9.455; 534/16

(58) Field of Classification Search .............. 424/9.3, 424/9.365, 1.11, 9.4, 9.45, 9.36, 9.364, 1.45, 424/1.65, 9.451, 9.453, 9.455; 534/16
See application file for complete search history.

(56) References Cited

U.S. PATENT DOCUMENTS

| 4,426,453 | A | * | 1/1984 | Cree et al. ................. 436/500 |
| 5,030,417 | A | * | 7/1991 | Spelsberg ................... 422/61 |
| 5,660,814 | A | * | 8/1997 | Uggeri et al. ............... 424/9.36 |
| 6,458,337 | B1 | * | 10/2002 | Anelli et al. ............... 424/9.36 |

OTHER PUBLICATIONS

Nina Boeing, et al., Endovascular Brachytherapy: Dosimetry . . . , Australasian Physical & Engineering Sciences in Medicine, vol. 24, pp. 63-70, 2001.
Tapas Das, et al., [186/188Re] Rhenium-Ethylene Dicysteine (Re-EC): Preparation . . . , Nuclear Medicine & Biology, vol. 27, pp. 189-197, 2000.
C.W. Joh, et al., Measurement of Radiation Absorbed Dose in Endovascular . . . , Nuclear Medicine Communications, vol. 21, pp. 959-964, 2000.
Kim HS, Cho YH, Kim JS, et al., Effect of Transcatheter Endovascular Radiation With Holmium-166 . . . , J Am Coll Cardiol, vol. 31, (supplA):277A, 1998.
Knapp, F. F. Jr., et al., Intraarterial Irradiation With Rhenium-188 Fir Inhibition . . . , J. Nucl. Med. vol. 38:124, 1997.
Majali MA, Studies on Preparation of Re-188-DTPA Complexes Using Low . . . , J. Radianal Nulc. Chem. vol. 170, No. 2, pp. 471-477, 1993.
Jin Lee, et al., Dosimetry of Rhenium-188 Diethylene . . . , European Journal of Nuclear Medicine, vol. 27, No. 1, 2000.
Wan-Yu Lin, MD., et al., Evaluation of Three Rhenium-188 Candidates . . . , J. Nucl. Cardiol. vol. 7, pp. 37-42, 2000.
Young-Don Hong, et al., Holmium-166 DTPA as a Liquid Source for Endovascular . . . , Nucl. Medicine and Biol., vol. 29, pp. 833-839, 2002.
M.A. Majali, et al., Potential 166 Ho Radiopharmaceuticals . . . , Nucl. Medicine Commun., vol. 22, pp. 97-103, 2001.
Mythili A. Majali, et al., Preparation and Evaluation of [166 Ho] Holmium-Dimethyl . . . , Applied Radiation and Isotopes, vol. 56, pp. 863-869, 2002.
Tapas Das, et al., Preparation and Animal Biodistribution of 166 Ho . . . , Journal of Labelled Compounds and Radiopharmaceuticals, J. Label Compd. Radiopharm, vol. 46, pp. 197-209, 2003.
Sudipta Chakraborty, et al., Potential 166 Ho Radiopharmaceuticals . . . , Nuclear Medicine and Biology, vol. 28, pp. 309-317, 2001.
Young-Don Hong, et al., The Availability of Contrast Media in the Application . . . , Nuclear Medicine and Biology, vol. 31, pp. 225-230, 2004.
Technetium Radiopharmaceuticals. In: Owunwanne A, Patel M, et al., The Handbook of Radiopharmaceuticals. Chapman & Hall Medical, pp. 57-105, 1995.
Yu SB, Watson AD., Metal-Based X-Ray Contrast Media, Chem. Rev., vol. 99, pp. 2353-2378, 1999.
Peter Caravan, et al., Gadolinium(III) Chelates As MRI . . . , Chem. Rev., vol. 99, pp. 2293-2352, 1999.

* cited by examiner

*Primary Examiner*—Michael G Hartley
*Assistant Examiner*—Leah Schlientz
(74) *Attorney, Agent, or Firm*—Lucas & Mercanti, LLP (57) ABSTRACT

The present invention relates to diethylenetriamine pentaacetic acid (DTPA) derivates and metal complexes thereof, and radiation sources and contrast agents including the metal complexes. More particularly, the present invention relates to DTPA derivatives, which contain iodine and are useful as contrast agents for diagnosing renal function, metal complexes of the DTPA derivatives with $^{99m}$Tc, $^{166}$Ho, $^{111}$In, $^{90}$Y, $^{153}$Sm, $^{186}$Re, $^{188}$Re, $^{68}$Ga, or $^{177}$Lu, which are useful as liquid radiation sources for treating vascular stenosis and contrast agents for diagnosing renal function, and radiation sources and contrast agents including the metal complexes. The DTPA derivatives and metal complexes thereof are safe because the metal complexes are excreted via the kidneys and bladder within several minutes from the time of use as liquid radiation sources for treating vascular stenosis, and are cost-effective because they are potentially useful as contrast agents and as agents for diagnosing renal function.

4 Claims, 7 Drawing Sheets

Fig. 1a

Stationary phase: ITLC-SG;   mobile phase: methylethylketone ($^{99m}$Tc-DTPA derivative and $^{99m}$TcO$_2$ at the origin, $^{99m}$TcO$_4^-$ at the solvent front)

Fig. 1b

Stationary phase: ITLC-SG;   mobile phase: saline

($^{99m}TcO_2$ at the origin, $^{99m}Tc$-DTPA derivative and $^{99m}TcO_4^-$ at the solvent front)

Fig. 2a

Stationary phase: ITLC-SA;   mobile phase: [methanol:water = 3:1 (v/v)]

Fig. 2b

Stationary phase: ITLC-SA; mobile phase: [methanol:water = 3:1 (v/v)]

($^{166}$Ho solution at the origin, $^{166}$Ho-DTPA derivative at the solvent front)

DTPA DERIVATIVES AND METAL COMPLEXES THEREOF, AND RADIATION SOURCE AND CONTRAST AGENT INCLUDING THE METAL COMPLEXES

This patent application claims the benefit of priority from Korean Patent Application No. 10-2005-0037062 filed May 3, 2005, the contents of which are incorporated herein by reference.

BACKGROUND OF THE INVENTION

1. Field of the Invention

The present invention relates to diethylenetriamine pentaacetic acid (DTPA) derivates and metal complexes thereof, and radiation sources and contrast agents including the metal complexes. More particularly, the present invention relates to DTPA derivatives, which contain iodine and are useful as contrast agents for diagnosing renal function, metal complexes of the DTPA derivatives comprising $^{99m}$Tc, $^{166}$Ho, $^{111}$In, $^{90}$Y, $^{153}$Sm, $^{186}$Re, $^{188}$Re, $^{68}$Ga, or $^{177}$Lu, which are useful as liquid radiation sources for treating vascular stenosis and contrast agents for diagnosing renal function, and radiation sources and contrast agents including the metal complexes.

2. Description of the Prior Art

Stenosis is the narrowing of blood vessels, and can occur in any area of the body, in which blood vessels are present, such as the cerebral vessels, cardiac vessels, peripheral vessels, and carotid arteries, due to fatty deposits, external stressors, hypertension, and the like. The use of liquid radiation sources for treating such vascular stenosis has the advantages of being cost-effective and of permitting the direct delivery of the uniform distribution of radiation to a site to be treated (Das T, Banerjee S, Samuel G, et al. [$^{186/188}$Re] rhenium-ethylene dicysteine (Re-EC): preparation and evaluation for possible use in endovascular brachytherapy. Nucl Med Biol 2000, 27:189-97; Joh C W, Park C H, Kang H J, et al. Measurement of radiation absorbed dose in endovascular Ho-166 brachytherapy using a balloon angiocatheter. Nucl Med Comm 2000, 21:959-64; Kim H S, Cho Y H, Kim J S, et al. Effect of transcatheter endovascular radiation with holmium-166 on neointimal formation after balloon injury in porcine coronary artery. J Am Coll Cardiol 1998, 31(supplA):277A).

Such therapy with liquid radiation sources, however, has the risk of balloon rupture, which is an unlikely event, but which leads to leakage of radioactive materials into the blood stream.

In order to prevent a patient from being overexposed to radiation in the event of balloon rupture, a variety of complexes of radioisotopes and chelating agents, which are not retained in the organs or the body but are rapidly excreted via the kidneys, have been developed. In the event of balloon rupture leading to radiation leakage, radiation sources for endovascular radiation brachytherapy for stenosis must have high in vivo stability and be retained in a minimum dose in major organs, and as well, they must be rapidly and completely excreted from the body via the kidneys.

Certain complexes of Re-188 with chelating agents, which include $^{188}$Re-DTPA, $^{188}$Re-MAG$_3$ (mercaptoacetylglycine$_3$) and $^{188}$Re-EC (ethylene dicysteine), have been developed. In such complex forms, Re-188 is observed to be rapidly excreted in urine (Knapp F F, Guhlke S, Beets A L, et al. Intraarterial irradiation with rhenium-188 for inhibition of restenosis after PTCA-Strategy and evaluation of species for rapid urinary excretion. J Nucl Med 1997, 38:124; Majali M A. Studies on the preparation of Re-188-DTPA complexes using low specific activity Re-186 for antibody labeling. J Radianal Nucl Chem 1993, 170:471; Lee J, Lee D S, Kim K M, et al. Dosimetry of rhenium-188 diethylene triamine penta-cetic acid for endovascular intra-balloon brachytherapy after coronary angioplasty. Eur J Nucl Med 2000, 27:76-82; Lin W Y, Tsai S C, Hsieh B T, et al. Wang Evaluation of three rhenium-188 candidates for intravascular radiation therapy with liquid-filled balloons to prevent restenosis. J Nucl Cardiol 2000, 7:37-42; Das T, Banerjee S, Samuel G, et al. [$^{186/188}$Re] rhenium-ethylene dicysteine (Re-EC): preparation and evaluation for possible use in endovascular brachytherapy. Nucl Med Biol 2000, 27:189-97).

Ho-166, which has radiochemical properties similar to those of Re-188, is advantageous in that its biodistribution can be readily imaged using a gamma camera because it emits both a maximum 1.85 MeV beta-ray and an 81 keV gamma-ray. Compared to Re-188, Ho-166 has the main advantage of being produced in the form of having high specific radioactivity at a high yield from naturally occurring Ho-165, making up 100% of the holmium on earth, through a nuclear reaction using a small-sized atomic reactor (Hong Y D, Park K B, Jang B S, et al. Holmium-166-DTPA as a liquid source for Endovascular brachytherapy. Nucl Med Biol 2002, 29:833-9; Majali M A, Saxena S K, Joshi S H, et al. Potential $^{166}$Ho radiopharmaceuticals for endovascular radionuclide therapy. II. Preparation and evaluation of $^{166}$Ho-DTPA. Nucl Med Comm 2001, 22:97-103).

Liquid radiation sources developed so far using Ho-166 include $^{166}$Ho-DTPA, $^{166}$Ho-DMDTPA (dimethyl diethylentriaminepentaacetic acid), $^{166}$Ho-DOTA (1,4,7,10-tetraazadodecane-N,N',N'',N'''-tetraacetic acid) and $^{166}$Ho-EC (Joh C W, Park C H, Kang H J, et al. Measurement of radiation absorbed dose in endovascular Ho-166 brachytherapy using a balloon angiocatheter. Nucl Med Comm 2000, 21:959-64; Majali M A, Mita, Debnath C, Saxena S K, Sangeeta H. Joshi Preparation and evaluation of [$^{166}$Ho] holmium-dimethyl diethylenetriaminepentaacetic acid (DMDTPA) as potential radiopharmaceutical for endovascular radiation therapy (EVRT). Appl Rad Isotopes 2004, 56:863-9; Das T, Chakraborty S, Banerjee S. Preparation and animal biodistribution of $^{166}$Ho labeled DOTA for possible use in intravascular radiation therapy (IVRT). J Label Compd Radiopharm 2003, 46:197-209; Chakraborty S, Unni P R, Banerjee S, et al. Potential $^{166}$Ho radiopharmaceuticals for intravascular radiation therapy (IVRT)-I: $^{166}$Ho labeled ethylene dicysteine. Nucl Med Biol 2001, 28:309-17).

The liquid radiation source $^{166}$Ho-DTPA is prepared through a simple procedure of mixing holmium and DTAP at pH 2-8 immediately before use. This simple procedure results in the formation of complexes having a high radiochemical purity greater than 98% (Hong Y D, Park K B, Jang B S, et al. Holmium-166-DTPA as a liquid source for Endovascular brachytherapy. Nucl Med Biol 2002, 29:833-9; Korean Pat. Registration No. 361091).

Upon angioplasty for treating cardiac vascular diseases with liquid radiation sources, which is commonly performed with computed tomography (CT) and angiography, the use of CT contrast agents, such as Hexabrix (320), Imeron (350) and Visipaque (320), permits the visual observation of the balloon interior to determine the presence of bubbles, which interrupt the precise delivery of a radiation dose to a site of cardiac vessels where stenosis occurs, and to determine whether the balloon is accurately positioned at a site to be treated so as to have a proper shape (Hong Y D, Choi S J, Choi S M, Jang B S. The availability of contrast media in the application of Holmium-166-DTPA for vascular brachytherapy. Nucl Med Biol 2004, 31:225-30).

However, when contrast agents are used as diluents, they have side effects including the formation of unknown complexes through a reaction with Ho-166, resulting in delayed or almost no excretion of the radionuclide from the body.

In addition, radiation imaging involves identifying specific pathological conditions or evaluating the severity of symptoms by injecting a contrast agent containing a radioisotope into the body and detecting the biodistribution of the contrast agent. Radionuclides, for use in the preparation of contrast agents in which a chelating agent is coordinate-bonded to a radionuclide, must satisfy the requirements of maximizing detection efficiency and minimizing a radiation dose absorbed by a patient. Thus, radionuclides emitting gamma radiation and having physical half-lives shorter than the imaging time are useful. $^{99m}$Tc (99m-technetium) is commonly used.

The diagnosis of renal diseases using $^{99m}$Tc is performed with dimercaptosuccinic acid (DMSA) for obtaining anatomical imaging and with GHA, DTPA, MAG$_3$ and EC for evaluating renal function (Technetium Radiopharmaceuticals. In: Owunwanne A, Patel M, Sadek S., The handbook of Radiopharmaceuticals. Chapman & Hall Medical 1995, 57-105).

In particular, the renal function is evaluated by assessing the excretion pattern of a radionuclide for a predetermined period of time using a gamma camera in order to obtain a renogram curve representing renal function. The use of complexes displaying rapid excretion patterns enhances detection efficiency and reduces detection time, thereby providing an economic benefit and ensuring accurate diagnosis.

Iodine compounds, including diatrizoate, ioxaglate, iohexol, and iodixanol, have been used as X-ray contrast agents. Metals, including gadolinium (Gd), tungsten (W), and lead (Pb), have been also used in the form of metal complexes. Imaging of these contrast agents is achieved using a computed tomography (CT) or angiography camera (Yu S B, Watson A D. Metal-Based X-ray Contrast Media. Chem. Rev. 1999, 99:2353-78).

Metal complexes of DTPA or DOTA with, for example, gadolinium (Gd), dysprosium (Dy), and manganese (Mn) are useful as contrast agents for magnetic resonance (MR) imaging (Caravan P, Ellison J J, McMurry T J, Lauffer R B. Gadolinium (III) Chelates as MRI Contrast Agents: Structure, Dynamics, and Applications. Chem. Rev. 1999, 99:2293-352).

At present, with the recent advances in imaging equipment, such as MR imaging, CT, angiography, CT/SPECT, and CT/PET, and the development and practical use of hybrid imaging equipment, there is a need for the development of complex compounds capable of accomplishing two or more purposes at one time.

In particular, there is a need for the development of contrast agents enabling real-time imaging upon angioplasty. In this regard, taking into account the fact that some DTPA derivatives easily react with radioisotopes, such as Re-188 and Ho-166, to form complexes, which can be used as liquid radiation sources in balloon angioplasty of vascular stenosis, and contain iodine, which is useful as a contrast agent for X-ray imaging, the present inventors synthesized complex compounds, which are useful as radiation sources for treating vascular stenosis and contrast agents, by binding DTPA derivatives and radioisotopes, thereby leading to the present invention.

The DTPA derivatives of the present invention may form complexes with gamma-emitting radionuclides, such as Tc-99m and In-111, which are quickly excreted in the urine, in order to minimize the patient's exposure to radiation, which is an unlikely event. Such complexes are useful as diagnostic agents for renal function because the radionuclides used can be imaged using a gamma camera. Also, the DTPA derivatives may be directly bound to gadolinium (Gd) so as to be used as contrast agents for MR imaging.

SUMMARY OF THE INVENTION

Therefore, the present invention aims to provide DTPA derivatives, which contain iodine and are useful as contrast agents for diagnosing renal function, metal complexes comprising the DTPA derivatives and $^{99m}$Tc, $^{166}$Ho, $^{111}$In, $^{90}$Y, $^{153}$Sm, $^{186}$Re, $^{188}$Re, $^{68}$Ga, or $^{177}$Lu, which are useful as liquid radiation sources for treating vascular stenosis and as contrast agents for diagnosing renal function, and radiation sources and contrast agents including the metal complexes.

The present invention provides a DTPA derivate represented by Chemical Formula 1, below, which is a chelating agent capable of binding to a metal including radionuclides.

[Chemical Formula 1]

wherein, R is selected from the group consisting of the following:

wherein, $R_1$ is H or $C_1$~$C_5$ alkyl.

In the chemical formula 1 of the present invention, it is preferable that the $R_1$ is H, $CH_3$ or $C_2H_5$.

The present invention also provides a DTPA derivate represented by Chemical Formula 2, below, which is a chelating agent capable of binding to a metal including radionuclides.

[Chemical Formula 2]

wherein, R and $R_1$ are the same as defined above.

The present invention further provides a metal complex of the compound of Chemical Formula 1, the metal complex being represented by Chemical Formula 3, below.

[Chemical Formula 3]

wherein, R and $R_1$ are the same as defined above, and M is selected from the group consisting of Y, Mn, Tc, Re, Ga, In, and lanthanide metals including Lu, Gd, Ho, Dy, Sm and La.

The present invention still further provides a metal complex of the compound of Chemical Formula 2, the metal complex being represented by Chemical Formula 4, below.

[Chemical Formula 4]

wherein, R and $R_1$ are the same as defined above, and M is selected from the group consisting of Y, Mn, Tc, Re, Ga, In, and lanthanide metals including Lu, Gd, Ho, Dy, Sm and La.

The present invention still further provides a liquid radiation source for use in the treatment of vascular stenosis, comprising a metal complex, which is prepared by reacting the DTPA derivate of Chemical Formula 1 or 2 with Y, Re, and lanthanide metals including Lu, Ho, Dy, and Sm.

The present invention still further provides a contrast agent for use in the diagnosis of renal function, comprising a metal complex, which is prepared by reacting the DTPA derivate of Chemical Formula 1 or 2 with metals including Tc, Ga, and In.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, the present invention will be described in detail.

The DTPA derivates according to the present invention are able to form metal complexes due to their high bonding strength to radioactive metals through coordinate bonding, and to easily bind to physiologically active substances. In detail, since the DTPA derivates according to the present invention have high bonding strength to metals because the carbonyl group, generated when a carboxyl group forms an amide bond with an amine group, has the ability to bind to metals, and have no risk of forming isomers between the derivatives, they do not decrease in labeling efficiency when used as contrast agents. Also, the iodine contained in the DTPA derivatives can be imaged using an X-ray generation source.

Thus, since the DTPA derivates according to the present invention are metal chelating agents, which have high bonding strength to metals, they form stable bonds with metals used in contrast agents.

The metal tetraacetate complex of Chemical Formula 3 according to the present invention is a metal complex generated when the DTPA derivative of Chemical Formula 1 is bonded to a metal. Since the carboxyl groups and carbonyl group of the DTPA derivative form stable bonds with the metal, this metal complex may be used as a contrast agent.

In addition, the metal tetraacetate complex of Chemical Formula 4 is a metal complex generated when the DTPA derivative of Chemical Formula 2 is bonded to a metal. Since the carboxyl groups and carbonyl group of the DTPA derivative form stable bonds with the metal, this metal complex may be used as a contrast agent.

The DTPA derivates of the present invention are prepared according to Reactions 1 and 2, below.

An amine group is converted into an amide group through amidation between the amine group and an anhydride. A DTPA anhydride is allowed to react with an amine group attached to a cyclic compound made up of a benzene-like ring containing iodine to provide the DTPA derivative of Chemical Formula 1 or 2. In Reaction 1, water is added.

[Reaction 1]

(Chemical Formula 1)

[Reaction 2]

(Chemical Formula 2)

In Reactions 1 and 2, L is identical to R having primary amine, which is defined in Chemical Formulas 1 and 2.

The amidation may be performed according to an ordinary method, including reacting a DTPA anhydrate with a compound containing an amino group under basic conditions.

Preferred bases include triethylamine (TEA), pyridine, and potassium carbonate ($K_2CO_3$). Inert solvents are suitable, and preferred solvents include dimethylformamide (DMF), and dimethylsulfoxide (DMSO).

In addition, the DTPA derivative of Chemical Formula 1 is allowed to react with a metal, selected from the group consisting of Y, Mn, Tc, Re, Ga, In, and lanthanide metals including Lu, Gd, Ho, Dy, Sm and La, in order to form the metal complex of Chemical Formula 3.

The DTPA derivative of Chemical Formula 2 is allowed to react with a metal, selected from the group consisting of Y, Mn, Tc, Re, Ga, In, and lanthanide metals including Lu, Gd, Ho, Dy, Sm and La, in order to form the metal complex of Chemical Formula 4.

The present invention still further provides contrast agents comprising the DTPA derivatives of Chemical Formulas 1 and 2, or the metal complexes of Chemical Formulas 3 and 4.

For use as contrast agents, the DTPA derivatives of Chemical Formulas 1 and 2 and the metal complexes of Chemical Formulas 3 and 4 may be provided as they are or in a kit form.

Since the contrast agents contain aqueous media along with the DTPA derivatives or metal complexes, they may be administered through intravenous injection. The media include commonly used pharmaceutical additives, such as pharmaceutically acceptable salts, buffers or antiseptics.

Since the DTPA derivatives contain iodine, which enables CT imaging, and have the ability to easily bind to gadolinium (Gd), which is a useful metal as a contrast agent for MR imaging, the DTPA derivatives and metal complexes thereof are useful as CT imaging agents and MR imaging agents.

In addition, when complexes of the DTPA derivatives with gamma-emitting radionuclides are administered to the body, their excretion patterns via the kidneys can be monitored, and their distribution in the body can be also analyzed. Thus, these metal complexes are useful as agents for diagnosing renal function in order to identify specific pathological conditions in the kidneys or to evaluate the severity of symptoms.

A better understanding of the present invention may be obtained through the following example which is set forth to illustrate, but is not to be construed as the limit of the present invention.

Example 1

Preparation of DTPA-mono(3-amido-2,4,6-triiodobenzoic acid)

10.0 g (25 mmol) of DTPA was dispersed in 20 ml of pyridine. 18 g (0.18 mol) of acetic anhydride was added to the dispersion, and a reaction was allowed to take place at 65□ for 24 hrs with stirring. After the reaction was completed, the reaction mixture was filtered to recover generated material. The recovered compound was washed with acetic anhydride and diethyl ether several times, and dried under pressure for 24 hrs, thereby obtaining a DTPA anhydride at a yield of 78%.

IR(cm$^{-1}$) 2979, 1820, 1774, 1641.

Then, 0.357 g (1 mmol) of the DTPA anhydride was added to 30 ml of anhydrous dimethylformamide (DMF), and mixed with stirring. This solution was supplemented with 0.515 g (1 mmol) of 3-amino-2,4,6-triiodobenzoic acid, and allowed to react at 60□ for 5 hrs with stirring. After the reaction was completed, the solvent was removed under pressure using an evaporator, and the remaining material was washed with ethanol and dried, thereby obtaining the desired product at a yield of 80%.

$^{1}$H NMR (D$_2$O+NaOD, ppm) 2.36 (m, 8H, CH$_2$CH$_2$), 2.80~2.90 (d, 10H, CH$_2$CO), 7.95 (s, 1H, Ar—H);

$^{13}$C NMR (D$_2$O+NaOD, ppm) 37.03, 52.05, 52.18, 58.89, 59.32, 74.93, 77.83, 80.44, 147.58, 153.27, 171.43, 180.04, 180.18;

IR (cm$^{-1}$) 3433, 1730, 1634, 1517, 1243.

Example 2

Preparation of DTPA-bis(3-amido-2,4,6-triiodobenzoic acid)

0.357 g (1 mmol) of the DTPA anhydride was added to 30 ml of anhydrous dimethylformamide (DMF), and mixed with stirring. This solution was supplemented with 0.13 g (2 mmol) of 3-amino-2,4,6-triiodobenzoic acid, and allowed to react at 60□ for 5 hrs with stirring. After the reaction was completed, the solvent was removed under pressure using an evaporator, and the remaining material was washed with ethanol and dried, thereby obtaining the desired product at a yield of 75%.

$^{1}$H NMR (D$_2$O+NaOD, ppm) 2.34 m, 8H, CH$_2$CH$_2$), 2.78~2.86 (d, 10H, CH$_2$CO), 7.92 (s, 2H, Ar—H).

Example 3

Preparation of DTPA-mono(2-amido-5-iodobenzoic acid)

The desired product was synthesized according to the same method as in Example 1 except that 2-amino-5-iodobenzoic acid (1 mmol) was used instead of the 3-amino-2,4,6-triiodobenzoic acid (1 mmol), and was obtained at a yield of 82%.

$^{1}$H NMR (D$_2$O+NaOD, ppm) 2.42 (m, 8H, CH$_2$CH$_2$), 2.87~2.93 (d, 10H, CH$_2$CO), 7.76~7.80 (m, 1H, Ar—H), 8.22~8.25 (m, 1H, Ar—H), 8.40 (d, 1H, Ar—H);

IR (cm$^{-1}$) 3429, 1725, 1637, 1508, 1233.

Example 4

Preparation of DTPA-bis(5-amido-2,4,6-triiodoisophthalic acid)

The desired product was synthesized according to the same method as in Example 1 except that 5-amino-2,4,6-triiodoisophthalic acid (2 mmol) was used instead of the 3-amino-2,4,6-triiodobenzoic acid (2 mmol), and was obtained at a yield of 80%.

$^{1}$H NMR (D$_2$O+NaOD, ppm) 2.47 (m, 8H, CH$_2$CH$_2$), 2.97~3.05 (d, 10H, CH$_2$CO);

$^{13}$C NMR (D$_2$O+NaOD, ppm) 37.03, 52.10, 52.18, 58.889, 59.31, 69.74, 75.48, 147.58, 153.98, 171.50, 177.12, 180.06, 180.19;

IR (cm$^{-1}$) 3443, 1724, 1635, 1517, 1223.

Example 5

Preparation of Complexes of the DTPA Derivatives with Radioactive Metal ($^{99m}$Tc)

Figure 1A:
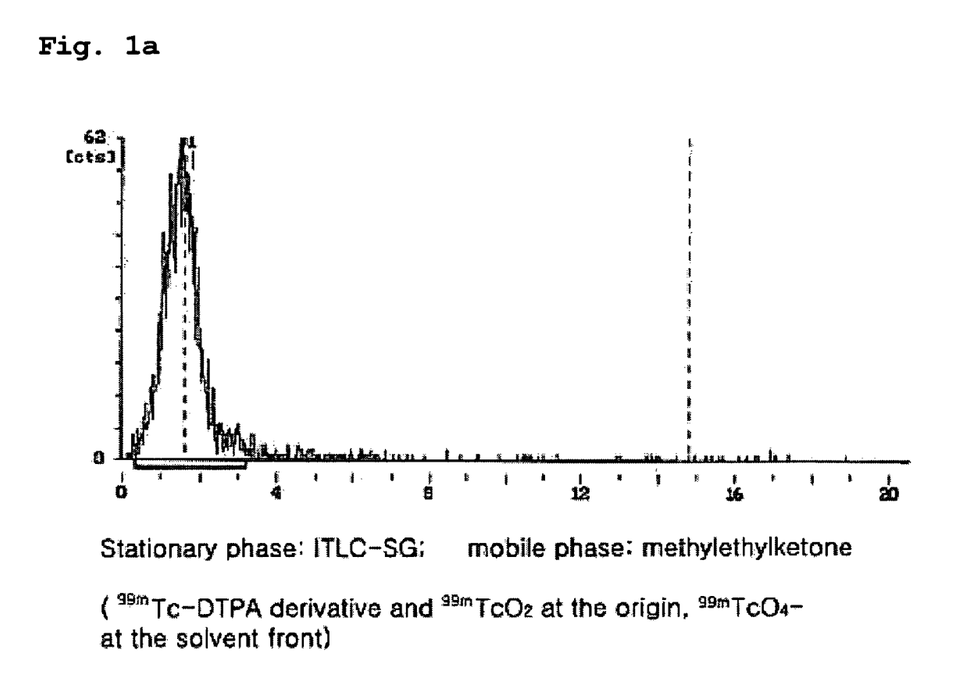
FIG. 1a shows the labeling efficiency of $^{99m}$Tc-DTPA-mono(3-amido-2,4,6-triiodobenzoic acid) according to the present invention, which was estimated using instant thin layer chromatography (ITLC) using ITLC-SG as a stationary phase and methylethylketone (MEK) as a mobile phase.
Figure 1B:
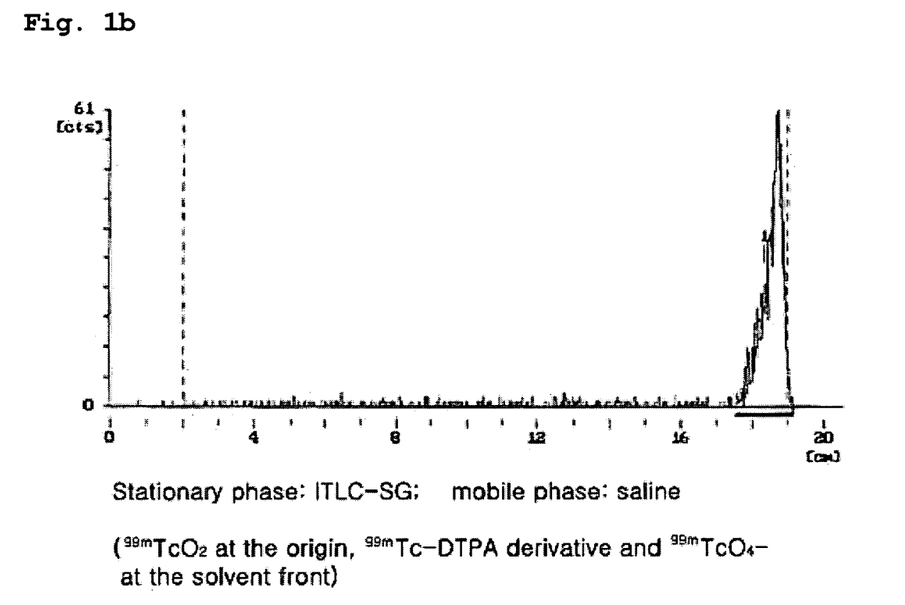
FIG. 1b shows the labeling efficiency of $^{99m}$Tc-DTPA-mono(3-amido-2,4,6-triiodobenzoic acid) according to the present invention, which was estimated using ITLC using ITLC-SG as a stationary phase and saline as a mobile phase.

20 mg of each of the DTPA derivatives prepared in Examples 1, 3 and 4, DTPA-mono(3-amido-2,4,6-triiodobenzoic acid) (MTIBA), DTPA-mono(2-amido-5-iodobenzoic acid) (MIBA) and DTPA-bis(5-amido-2,4,6-triiodoisophthalic acid) (BTIIPA), was mixed with 0.4 mg of stannous chloride (SnCl$_2$) to provide a solution. Each solution was adjusted to a pH from 4 to 6. 1 ml of $^{99m}$TcO$_4^-$ (10 mCi/ml) was added to 1 ml of each of the prepared solutions, and a labeling reaction was allowed to take place at room temperature for 30 min. The resulting reaction solutions were developed using instant thin layer chromatography-silica gel paper (ITLC-SG paper) as a stationary phase and methyethylketone (MEK) (FIG. 1a) and saline (FIG. 1b) as mobile phases. The radiolabeling yield was determined using an ITLC scanner according to the following equation: Radiolabeling Yield (%)=100×[(% of $^{99m}$TcO$_4^-$)−(% of $^{99m}$TcO$_2$)]. As a result, all compounds were found to be labeled with $^{99m}$Tc at a yield of greater than 95%.

TABLE 1

| $^{99m}$Tc-complexes | Radiolabeling yields |
|---|---|
| $^{99m}$Tc-DTPA-BTIIPA | >95% |
| $^{99m}$Tc-DTPA-MTIBA | >95% |
| $^{99m}$Tc-DTPA-MIBA | >95% |

Example 6

Preparation of Complexes of the DTPA Derivative with Radioactive Metal ($^{188}$Re)

20 mg the DTPA derivative prepared in Example 1, DTPA-mono(3-amido-2,4,6-triiodobenzoic acid), was mixed with 5 mg of stannous chloride ($SnCl_2$) to provide a solution. The solution was adjusted to a pH from 5 to 6. 1 ml of $^{188}ReO_4^-$ (5 mCi/ml) was added to 1 ml of the prepared solution, and a labeling reaction was allowed to take place at 100□ for 30 min. The resulting reaction solution was developed using ITLC-SG paper as a stationary phase and methyethylketone (MEK) and saline as mobile phases. The radiolabeling yield was determined using an ITLC scanner (EG&G Berthold Linear Analyzer). As a result, the resulting compound was found to be labeled with $^{188}$Re at a yield of greater than 90%.

Example 7

Preparation of Complexes of the DTPA Derivatives with Radioactive Metal ($^{166}$Ho)

Figure 2A:
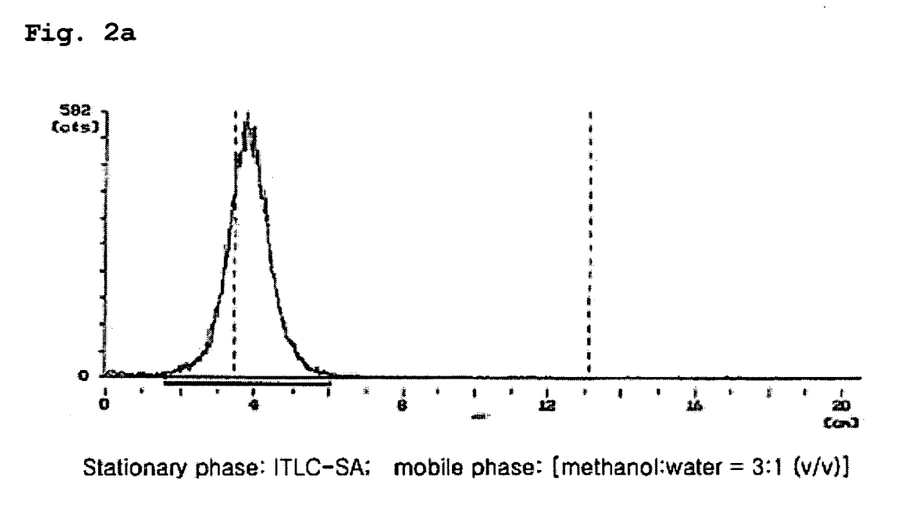
FIG. 2a shows the results of ITLC for a $^{166}$Ho solution according to the present invention.

A $^{166}$Ho solution was developed using instant thin layer chromatography-silicic acid (ITLC-SA) as a stationary phase and a 3:1 (v/v) mixture of methanol and water as a mobile phase (FIG. 2a).

Figure 2B:
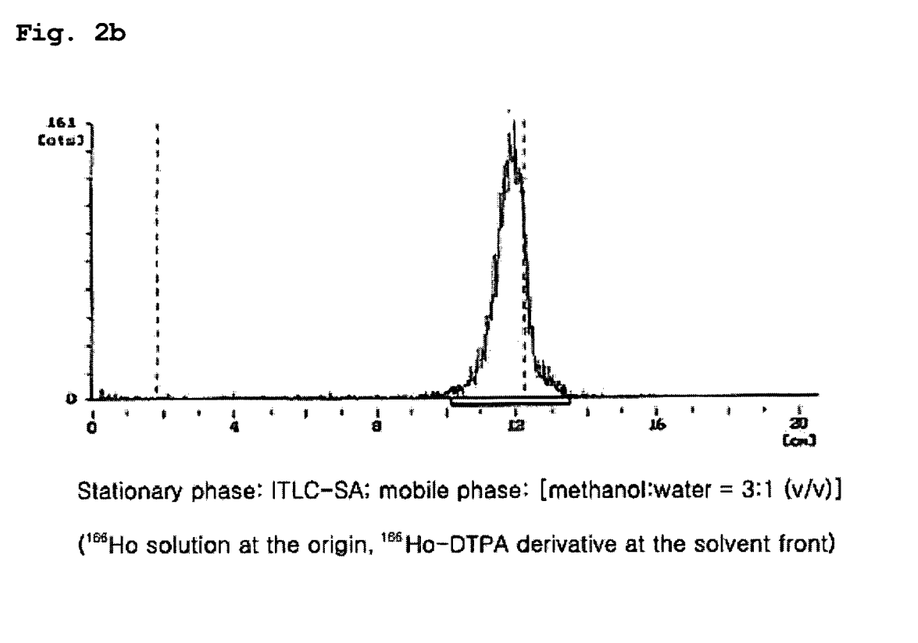
FIG. 2b shows the labeling efficiency of a $^{166}$Ho-DTPA derivative complex according to the present invention, which was estimated using ITLC.

A solution, containing 20 mg of each of the DTPA derivatives prepared in Examples 1, 3 and 4, DTPA-mono(3-amido-2,4,6-triiodobenzoic acid) (MTIBA), DTPA-mono(2-amido-5-iodobenzoic acid) (MIBA) and DTPA-bis(5-amido-2,4,6-triiodoisophthalic acid) (BTIIPA), was prepared. Each solution was adjusted pH 5 to 6. 30 mCi of $^{166}$Ho-nitrate (HCl solution (pH 2.8~3.0) was added to 1 ml of each of the prepared solutions, and a labeling reaction was allowed to take place at room temperature for 15 min. The resulting reaction solutions were developed using instant thin layer chromatography-silicic acid (ITLC-SA) as a stationary phase and a 3:1 (v/v) mixture of methanol and water as a mobile phase (FIG. 2b). The radiolabeling yield was determined using an ITLC scanner (EG&G Berthold Linear Analyzer).

As a result, all compounds were found to be labeled with $^{166}$Ho at a yield of greater than 98%.

TABLE 2

| $^{166}$Ho-complexes | Radiolabeling yields | Rf values [ITLC-SG & methal:water (3:1, v/v) |
|---|---|---|
| Ho-166 solution | — | 0 |
| $^{166}$Ho-DTPA-BTIIPA | 100% | 0.9-1.0 |
| $^{166}$Ho-DTPA-MTIBA | 100% | 0.9-1.0 |
| $^{166}$Ho-DTPA-MIBA | 100% | 0.9-1.0 |

Example 8

Preparation of Complexes of the DTPA Derivatives with Metal (Gd)

Gd-DTPA-mono(3-amido-2,4,6-triiodobezoic acid) was prepared as follows. The DTPA derivative prepared in Example 1, DTPA-mono(3-amido-2,4,6-triiodobenzoic acid), was mixed with the same molar equivalent of gadolinium chloride ($GdCl_3$) to provide a solution ranging from pH 5 to 6. The solution was stirred at room temperature for 24 hrs and finally adjusted to a pH value of about 7.3. The resulting reaction solution was added into a sodium acetate/acetic acid buffer (NaAc/HOAc buffer, pH 5.5), and non-reacted gadolinium (Gd) ions were detected using a calorimetric method with xylenol orange. As a result, non-reacted gadolinium (Gd) was not detected.

Test Example 1

Figure 3A:
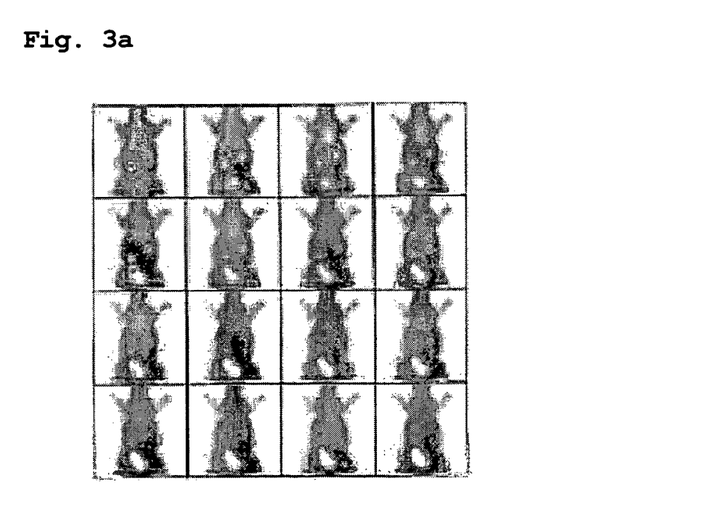
FIGS. 3a and 3b show time activity curves which were obtained when regions of interest (ROIs) were created around the right and left kidneys of rabbits receiving a $^{99m}$Tc-DTPA derivative complex according to the present invention.
Figure 3B:
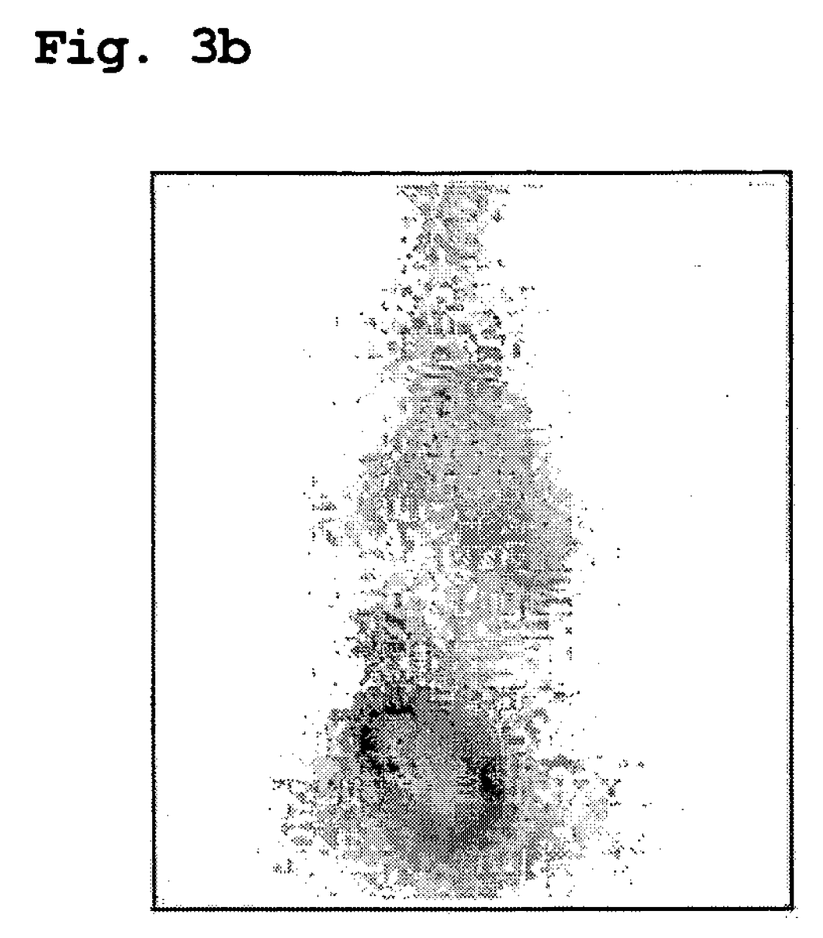

Evaluation of the Urinary Excretion of the Radioactive Metal ($^{99m}$Tc) Complex According to the Present Invention in Animals Male rabbits (New Zealand White) were anesthetized by the intramuscular injection of 25 mg/kg of Ketamine (Yuhan Corporation, Korea) and 6 mg/kg of Rompun (Bayer Korea), and then received through the ear vein 1.0±0.1 mCi of the $^{99m}$Tc-DTPA derivative complex, $^{99m}$Tc-DTPA-mono(3-amido-2,4,6-triiodobenzoic acid). The behavior of the drug was monitored for 30 min by scanning the whole body of rabbits using a gamma camera (SIMENSE, Germany). The gamma camera was equipped with a parallel hole collimator, and was set at an energy level of 140 keV to obtain images. The results are given in FIGS. 3a and 3b. As shown in FIGS. 3a and 3b, the $^{99m}$Tc-DTPA-mono(3-amido-2,4,6-triiodobezoic acid) was mostly excreted via the kidneys and bladder within 30 min from injection.

Figure 4:
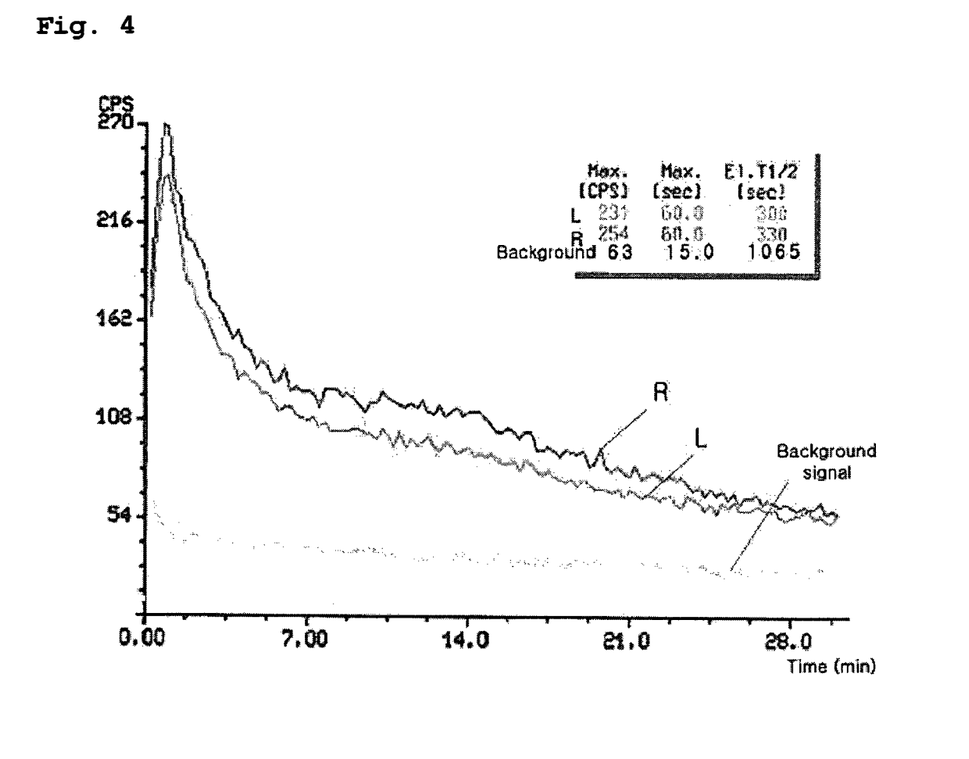
FIG. 4 shows the time to achieve maximum activity ($T_{max}$) and time to eliminate half of the maximum activity ($T_{1/2}$) for each kidney, which were calculated from the time activity curves of FIGS. 3a and 3b using a computer system.

In addition, regions of interest (ROIs) were created around the right and left kidneys to produce time activity curves. From the time activity curves, time to achieve maximum activity ($T_{max}$) and time to eliminate half of the maximum activity ($T_{1/2}$) for each kidney were calculated using a computer system (SINCTRON IV, Germany), and the results are given in FIG. 4. As shown in FIG. 4, the radioactivity in the kidneys was found to decrease to a level near the non-specific background signal 30 min after injection, indicating that the $^{99m}$Tc-complex was rapidly excreted in urine. The $T_{max}$ and $T_{1/2}$ values were found to be 1 min and 5 min for the left kidney and 1 min and 5.5 min for the right kidney. These results indicate that the $^{99m}$Tc-DTPA-mono(3-amido-2,4,6-triiodobezoic acid) was mostly excreted via the kidneys and bladder within 30 min from injection.

Test Example 2

Figure 5A:
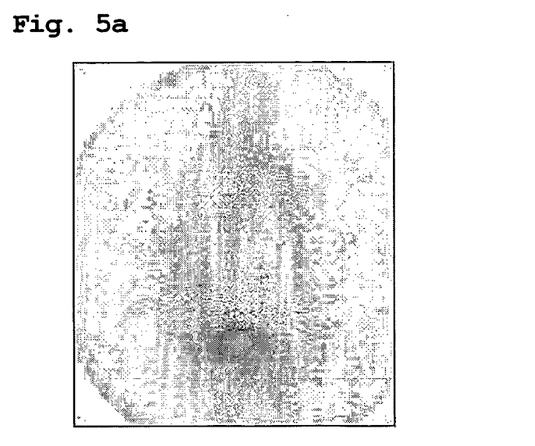
FIGS. 5a and 5b are images of the right and left kidneys of rabbits receiving a $^{166}$Ho-DTPA derivative complex according to the present invention, wherein the images were obtained using a gamma camera equipped with a medium-energy collimator with a window width of 20%.
Figure 5B:
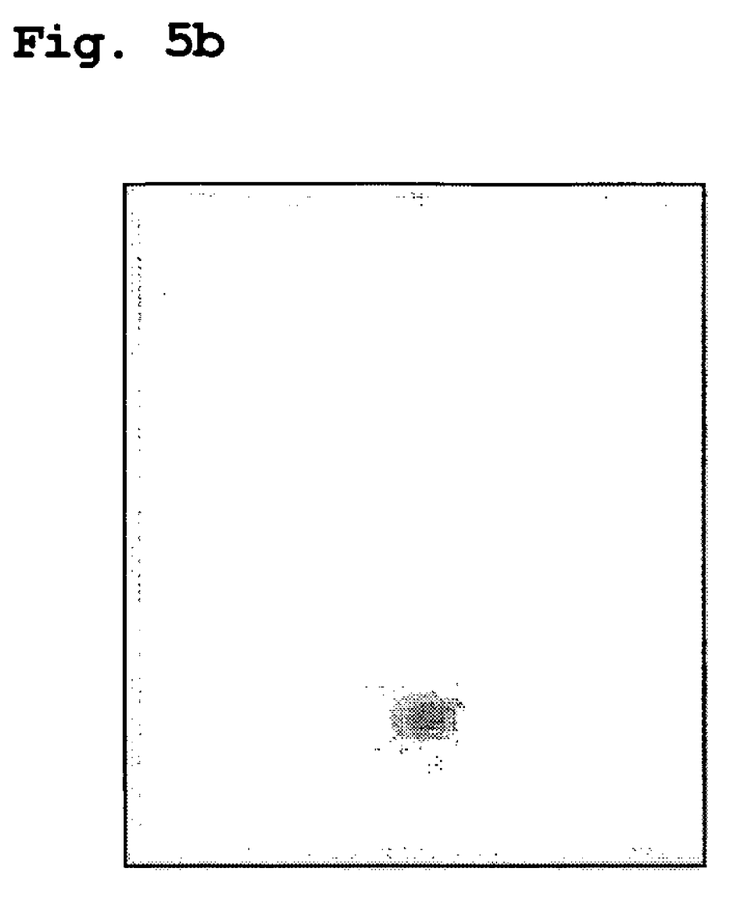

Evaluation of the Urinary Excretion of the Radioactive Metal ($^{166}$Ho) Complex According to the Present Invention in Animals Male rabbits (New Zealand White) were anesthetized by intramuscular injection of 25 mg/kg of Ketamine (Yuhan Corporation, Korea) and 6 mg/kg of Rompun (Bayer Korea), and then received through the ear vein 3.0±0.2 mCi of $^{166}$Ho-DTPA-bis(5-amido-2,4,6-triiodoisophthalic acid). The behavior of the drug was monitored for 30 min by scanning the whole body of rabbits using a gamma camera (SIMENSE, Germany). The gamma camera was equipped with a parallel hole collimator, and was set at an energy level of 81 keV. At this energy level, images were obtained using a medium-energy collimator with a window width of 20%. The results are given in FIGS. 5a and 5b. As shown in FIGS. 5a and 5b, the $^{166}$Ho-DTPA-bis(5-amido-2,4,6-triiodoisophthalic acid) was mostly excreted via the kidneys and bladder within 30 min from injection.

Figure 6:
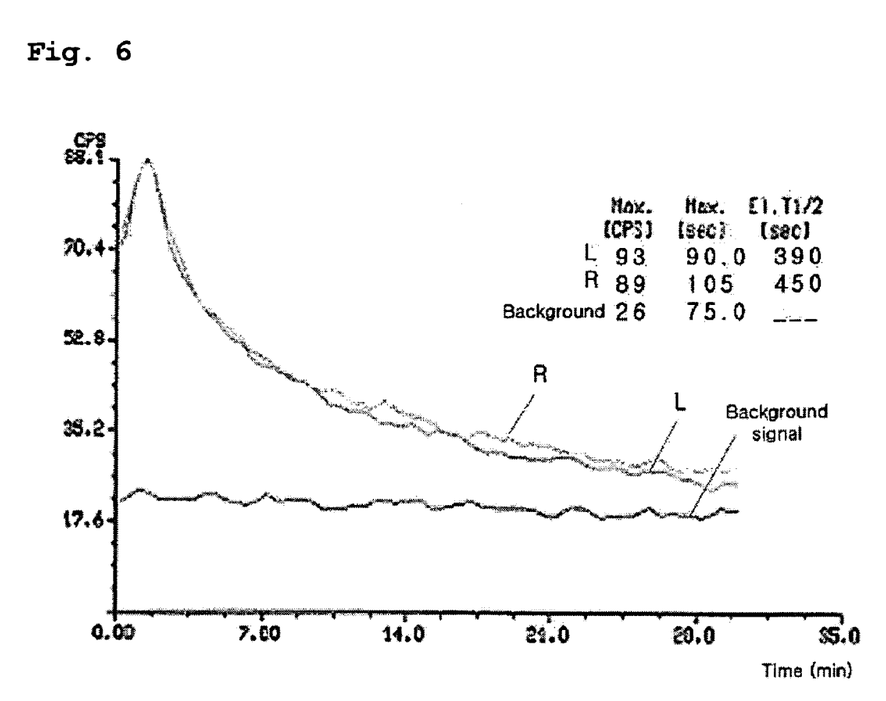
FIG. 6 shows the $T_{max}$ and $T_{1/2}$ for each kidney, which were calculated from the time activity curves of FIGS. 5a and 5b using a computer system.

In addition, regions of interest (ROIs) were created around the right and left kidneys to produce time activity curves. From the time activity curves, time to maximum activity ($T_{max}$) and half time of the maximum activity ($T_{1/2}$) for each kidney were calculated using a computer system (SINC- TRON IV, Germany), and the results are given in FIG. 6. As shown in FIG. 6, the radioactivity in the kidneys was found to decrease to a level near the non-specific background signal 30 min after injection, indicating that the [166]Ho-DTPA-bis(5-amido-2,4,6-triiodoisophthalic acid) was rapidly excreted in urine. The $T_{max}$ and $T_{1/2}$ values were found to be 1.5 min and 6.5 min for the left kidney and 1.75 min and 7.5 min for the right kidney. These results indicate that the [166]Ho-DTPA-bis (5-amido-2,4,6-triiodoisophthalic acid) was mostly excreted via the kidneys and bladder within 30 min from injection.

Although a preferred embodiment of the present invention has been described for illustrative purposes, the scope of the present invention is not specifically limited to the examples, and those skilled in the art will appreciate that various modifications, additions and substitutions are possible, without departing from the scope and spirit of the invention as disclosed in the accompanying claims.

As described hereinbefore, when the DTPA derivatives of the present invention form metal complexes with beta-emitting radionuclides, they display rapid excretion patterns via the kidneys. Thus, the metal complexes of the DTPA derivatives are safe and useful as liquid radiation sources for treating vascular stenosis.

In addition, since the DTPA derivatives contain iodine, which enables CT imaging, and have the ability to easily bind to a metal, gadolinium (Gd), which is useful as a contrast agent for MR imaging, the DTPA derivatives and metal complexes thereof are useful both as CT imaging agents and as MR imaging agents, and thus are cost-effective.

Further, when complexes of the DTPA derivatives with gamma-emitting radionuclides are administered to the body, their excretion patterns via the kidneys can be monitored, and their distribution in the body can be also analyzed. Thus, these metal complexes are useful as diagnostic agents for renal function to identify specific pathological conditions in the kidneys or to evaluate the severity of symptoms.

What is claimed is:

1. A metal complex represented by Chemical Formula 4,

[Chemical Formula 4]

wherein
R is selected from the group consisting of:

wherein, $R_1$ is H, $CH_3$ or $C_2H_5$; and

M is selected from the group consisting of Y, Re, Lu, Ho, Dy, and Sm.

2. A method for treating vascular stenosis in a mammal comprising administering a liquid radiation source comprising a metal complex represented by Chemical Formula 3 to a mammal having vascular stenosis,

[Chemical Formula 3]

wherein
R is selected from the group consisting of:

wherein
R is selected from the group consisting of:

wherein, $R_1$ is H, $CH_3$ or $C_2H_5$; and
M is selected from the group consisting of $^{90}$Y, $^{186}$Re, $^{188}$Re, $^{177}$Lu, $^{166}$Ho, and $^{153}$Sm.

3. A method for treating vascular stenosis in a mammal comprising administering a liquid radiation source comprising a metal complex represented by Chemical Formula 4 to a mammal having vascular stenosis,

[Chemical Formula 4]

wherein, $R_1$ is H, $CH_3$ or $C_2H_5$; and

M is selected from the group consisting of $^{90}$Y, $^{186}$Re, $^{188}$Re, $^{177}$Lu, $^{166}$Ho, and $^{153}$Sm.

4. The metal complex of claim 1, wherein Y is $^{90}$Y, Re is $^{186/188}$Re, Lu is $^{177}$Lu, Ho is $^{166}$Ho, and Sm is $^{153}$Sm.

* * * * *